US009757563B2

United States Patent
Roy et al.

(10) Patent No.: US 9,757,563 B2
(45) Date of Patent: *Sep. 12, 2017

(54) NEURAL STIMULATION FOR INCREASED PERSISTENCE

(71) Applicant: Second Sight Medical Products, Inc., San Fernando, CA (US)

(72) Inventors: Arup Roy, Valencia, CA (US); Robert Greenberg, Los Angeles, CA (US); Mark Humayan, Glendale, CA (US); Kelly McClure, Simi Valley, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/880,830

(22) Filed: Oct. 12, 2015

(65) Prior Publication Data

US 2016/0030745 A1 Feb. 4, 2016

Related U.S. Application Data

(62) Division of application No. 11/506,619, filed on Aug. 17, 2006, now Pat. No. 9,186,507, which is a division of application No. 11/044,761, filed on Jan. 26, 2005, now Pat. No. 7,571,004.

(51) Int. Cl.
*A61N 1/00* (2006.01)
*A61N 1/36* (2006.01)

(52) U.S. Cl.
CPC ................ *A61N 1/36046* (2013.01)

(58) Field of Classification Search
CPC .... A61N 1/36; A61N 1/36046; A61N 1/3605; A61N 1/36135; A61N 1/36139; A61N 1/36185

See application file for complete search history.

(56) References Cited

U.S. PATENT DOCUMENTS

| | | |
|---|---|---|
| 4,573,481 A | 3/1986 | Bullara |
| 4,628,933 A | 12/1986 | Michelson |
| 4,837,049 A | 6/1989 | Byers |
| 5,109,844 A | 5/1992 | de Juan, Jr. |
| 5,215,088 A | 6/1993 | Normann |
| 5,935,155 A | 8/1999 | Humayun |
| 5,944,747 A | 8/1999 | Greenberg |
| 6,400,989 B1 | 6/2002 | Eckmiller |
| 6,458,157 B1 | 10/2002 | Suaning |
| 6,507,758 B1 | 1/2003 | Greenberg |
| 6,533,798 B2 | 3/2003 | Greenberg |
| 2002/0010496 A1 | 1/2002 | Greenberg |
| 2002/0022866 A1* | 2/2002 | Borkan ............... A61N 1/056 607/59 |

* cited by examiner

*Primary Examiner* — Scott Getzow
(74) *Attorney, Agent, or Firm* — Scott Dunbar

(57) ABSTRACT

The present invention is a method of improving the persistence of electrical neural stimulation, and specifically a method of improving the persistence of an image supplied to a retina, or visual cortex, through a visual prosthesis. A continuously stimulated retina, or other neural tissue, will desensitize after a time period in the range of 20 to 150 seconds. However, an interruption of the stimulation on the order of a few milliseconds will restore the retinal sensitivity without the user perceiving the interruption, or with the user barely perceiving the interruption.

8 Claims, 4 Drawing Sheets

NEURAL STIMULATION FOR INCREASED PERSISTENCE

CROSS-REFERENCE TO RELATED APPLICATIONS

This patent application is a divisional application of U.S. patent application Ser. No. 11/506,619, filed Aug. 17, 2006, for Neural Stimulator for Increased Persistence, which is a divisional application of U.S. patent application Ser. No. 11/044,761, filed Jan. 26, 2006 for Neural Stimulator for Increased Persistence, the disclosures of which is incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of neural stimulation for improved persistence.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across retinal neuronal cell membranes, which can initiate retinal neuronal action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the retinal neurons, and avoid undue compression of the retinal neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated a cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

It is known that neurons respond best to change in stimuli. The retina, if continuously stimulated in a consistent manner, will slowly become less and less sensitive to the stimulus. This causes the perception of a constant visual image to gradually disappear. Those with normal vision are unable to perceive this effect because the eye constantly moves, motions called jitter or microsaccades. A normal retina has a resolution of approximately four million light transducer cells (rods and cones), hence it requires a minute movement to change the light intensity cast upon a given light transducer.

A retinal prosthesis, according to the present invention, has two disadvantages. First, the resolution of an electrode array applied to the retina, is significantly lower than the resolution of a healthy retina, requiring a greater movement to move an image from one electrode to the next electrode, as compared to one cone to the next cone. Further, a head mounted camera does not have the natural jitter or microsaccades of an eye. Therefore it is necessary to achieve the required change in another manner.

It is also known that some neural processing is done within the retina. Hence, a continuously stimulated cone will not result in a continuous signal to the brain. Ganglion and bipolar cells pass along this change in information more readily than constant information. In a diseased retina, rods and cone can not be stimulated, since they are dead. Electrically stimulating cells further along the neural pathway, bypasses some of the neural processing. This processing must be simulated electronically to gain normal brain stimulation.

The ability to perceive a constant image or image persistence is necessary to the design of a visual prosthesis.

SUMMARY OF THE INVENTION

The present invention is a method of improving the persistence of electrical neural stimulation, and specifically a method of improving the persistence of an image supplied to the retina, or visual cortex, through a visual prosthesis. A continuously stimulated retina, or other neural tissue, will adapt or desensitize after a time period in the range of 20 to 150 seconds. However, an interruption of the stimulation on the order of a few milliseconds will restore the retinal sensitivity without the user perceiving the interruption, or with the user barely perceiving the interruption.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
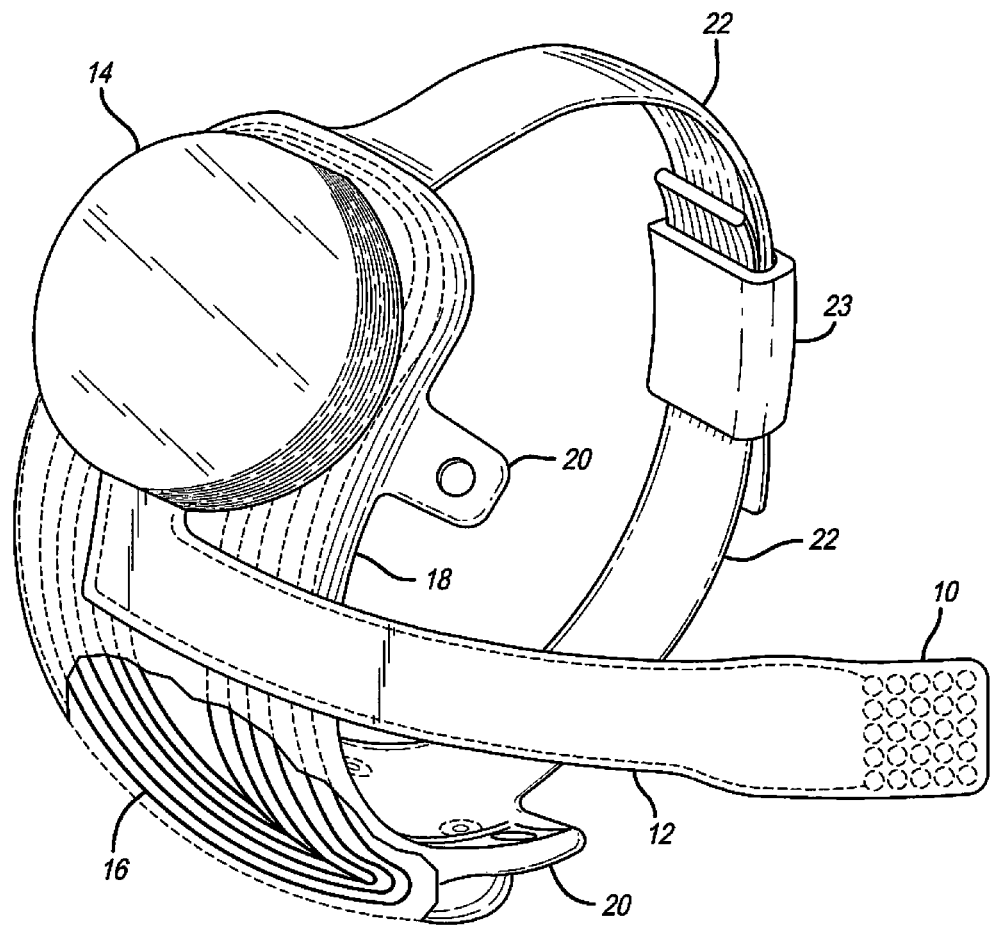
FIG. 1 is a perspective view of the implanted portion of the preferred retinal prosthesis.

FIG. 1 shows a perspective view of the implanted portion of the preferred retinal prosthesis. An electrode array 10 is mounted by a retinal tack or similar means to the epiretinal surface. The electrode array 10 is electrically coupled by a cable 12 which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil may be made from a thin film polymer sandwich with wire traces deposited between layers of thin film polymer. The electronics package 14 and secondary inductive coil 16 are held together by a molded body 18. The molded body 18 may also include suture tabs 20. The molded body narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. It is an advantage of the present design, that the entire implanted portion of the prosthesis is attached to and supported by the sclera. By placing the device under the rectus muscles with the electronics package in an area of fatty issue between the rectus muscles, eye motion does not cause any flexing which might fatigue, and eventually damage, the device.

Figure 2:
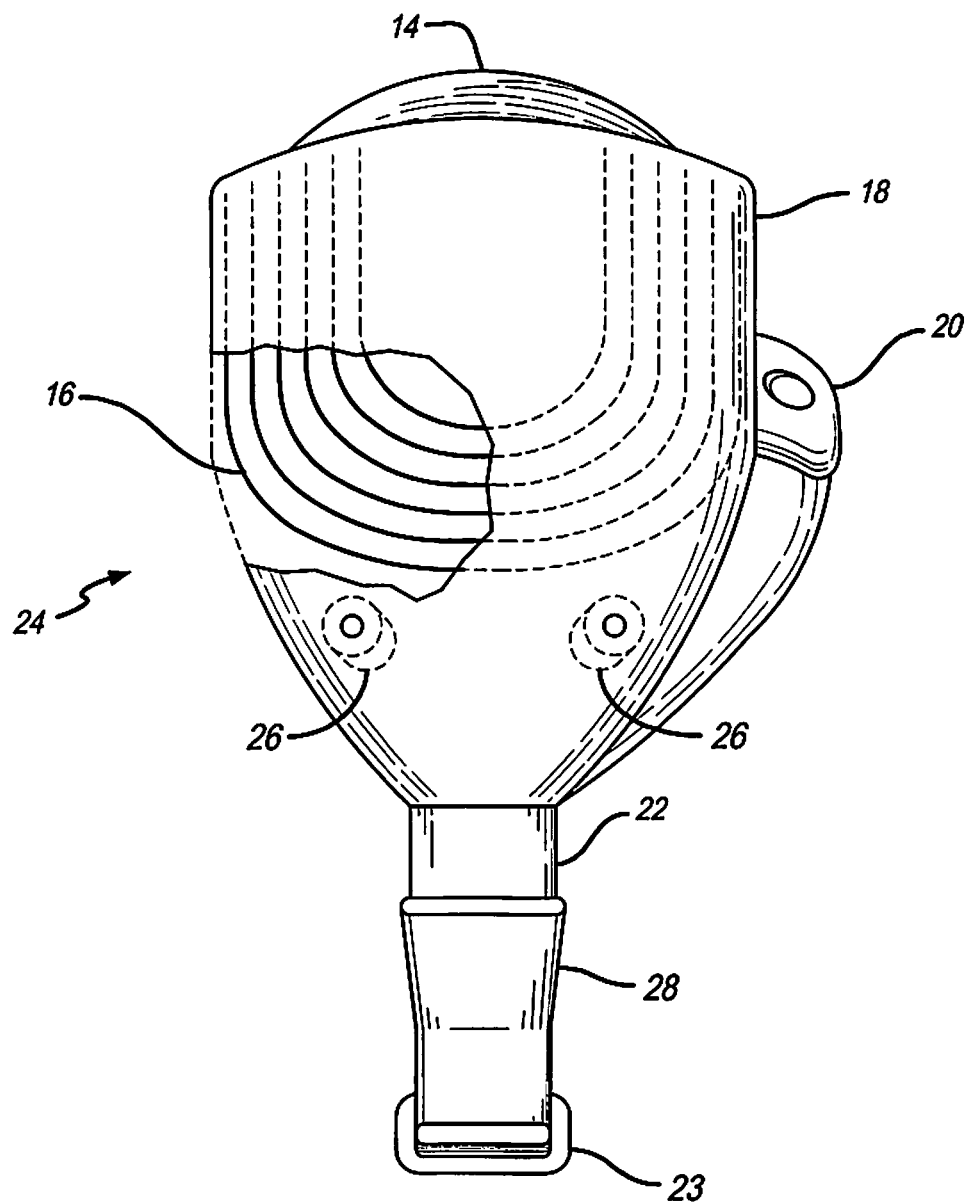
FIG. 2 is a side view of the implanted portion of the preferred retinal prosthesis showing the fan tail in more detail.

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body is shaped in the form of a fan tail 24 on the end opposite the electronics package 14.

Figure 3:
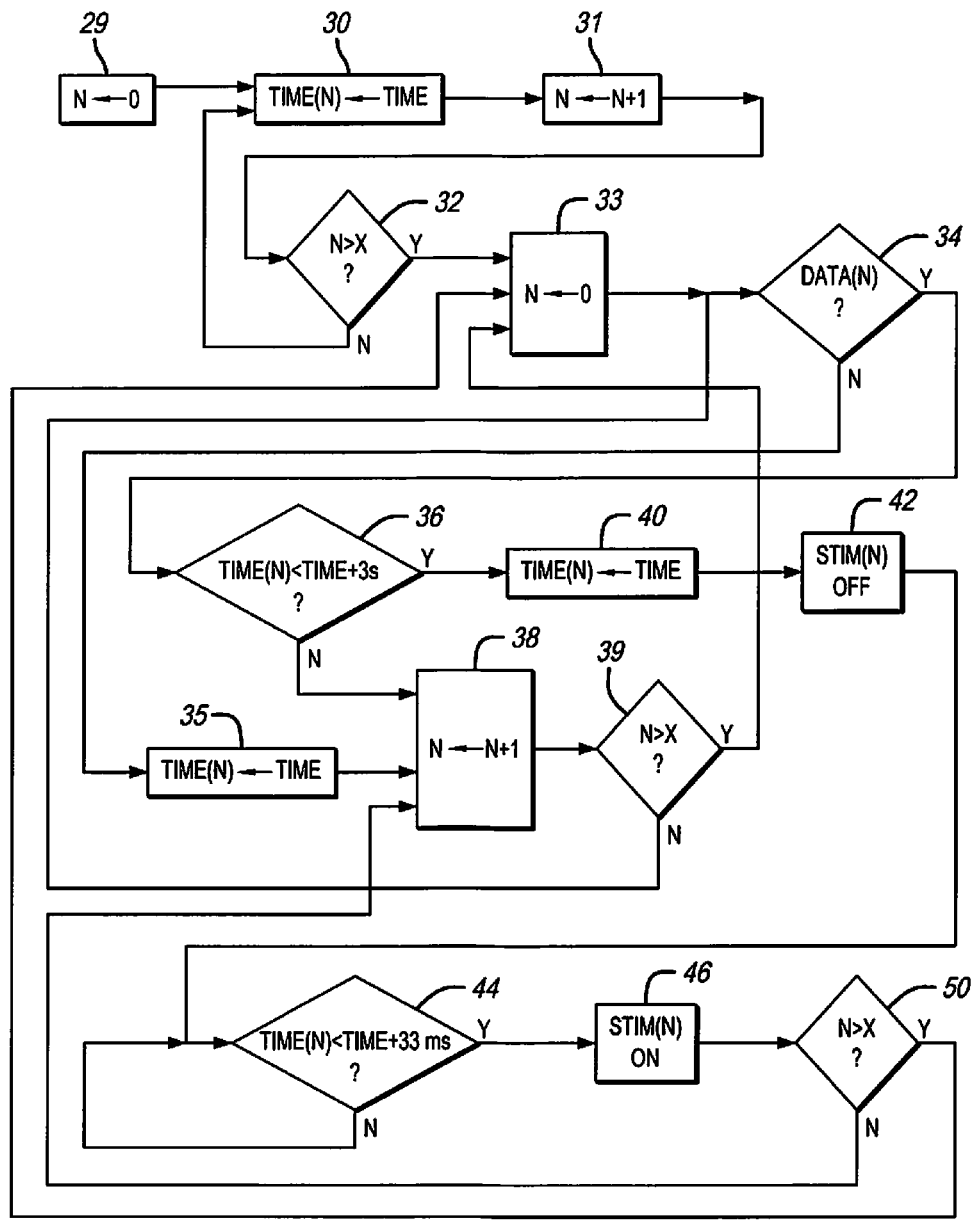
FIG. 3 depicts a flow chart showing the processing in the preferred embodiment.

FIG. 3 is a flow chart showing the basic operation of the periodic interruption scheme. The process must cycle through each electrode so that each electrode is interrupted, but not all electrodes are interrupted simultaneously. Hence the system begins with an initialization loop storing the current time in an array of values for each electrode. Time must be tracked for each electrode independently, so the array of time values, time(N) stores time values for each electrode. The electrode counter N is set to zero 29. The current time (time) is loaded into the array at time(N) 30, and N is incremented 31. As long as N is less than the total number of electrodes, X the loop repeats 32. The electrode counter, N is set to zero again in step 33. Next the system tests for data on electrode N. If no data, or sub-threshold data, causes electrode N to cease stimulation 34, there is no need to interrupt, and the current time is reset in time(N) 35, and N is incremented to address the next electrode 38. Interruption in the data occurs naturally on a regular basis such as scanning across a dark corner in a room. In the total number of electrodes (X) has not been exceeded 39, the process continues on the next electrode 34. If the total number has been exceeded, 39 the electrode counter is reset 33. If there is data, an interruption may be needed. In the preferred embodiment, the longest continuous stimulation is three seconds. Step 34 compares the current time with the stored time(N) plus three seconds. If three seconds have not elapsed, N is incremented in step 38 and the system checks for data on the next electrode 34.

When an electrode has stimulated continuously for more than 3 seconds 36, time(N) is reset and stimulation for that electrode is interrupted 42. 33 milliseconds are counted out 44 and stimulation resumes 46. This process continues until each electrode has been interrupted 50. The system compares N to X, the total number of electrodes and once all electrodes have been interrupted, at which point N is reset to zero in step 30.

While a simple raster pattern is the simplest method of selecting electrodes it does not achieve the best response. It is preferable to not interrupt adjacent electrodes near the same time. A pattern that jumps around the electrode array will achieve a better result. Ideally, a pseudorandom generator constantly varies the interruption pattern. This, however, requires a lot of processing power. Establishing a pseudorandom pattern in advance and repeating the pattern will achieve good results and require less processing power.

Depending on the time values selected (interruption time and time between interruptions) and the total number of electrodes, it may be necessary to interrupt more than one electrode at a time. In the preferred embodiment, there is a thee second stimulation period and a thirty three millisecond interruption period, or a ratio of about one hundred to one. Hence, nearly one hundred electrodes can be interrupted sequentially within a stimulation period, with a small allowance for processing time. If the array has more than one hundred electrodes, more than one electrode will need to be interrupted simultaneously. However, the smallest number of electrodes interrupted simultaneously will result in the least likelihood of the user noticing the interruption. If more than one electrode is to be interrupted at a time, it would be advantageous to organize the electrodes by zone, interrupting only one electrode at a time in each zone, thus reducing the likelihood that adjacent electrodes will be interrupted simultaneously.

Figure 4:
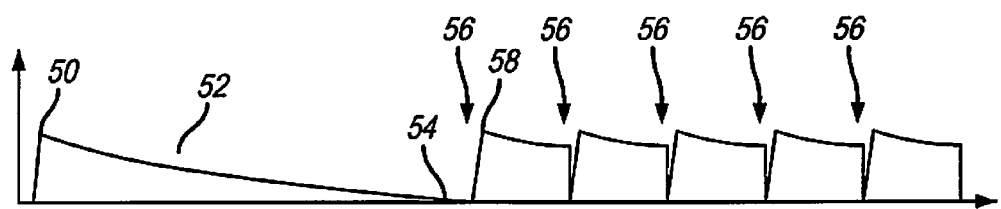
FIG. 4 depicts a typical perceptual pattern for a single electrode.

Referring to FIG. 4, a typical perceptual response to a constant stimulus begins to decay immediately. A stimulus creates a percept 50 that gradually decays 52 until the precept disappears, 54. An interruption of the stimulus, 56 brings the precept back to a full response 58 and decay begins again. Hence, the more often stimulation is interrupted, the more natural the perceived response will be. However, the more often stimulation is interrupted, the more likely a user is to notice the interruption. This is especially true if multiple electrodes are interrupted at the same time. Since, each individual's ability to perceive the interruptions varies, as well as each individual's persistence response decay varies, it is advantageous to have both periods, stimulation and interruption, programmable to achieve optimal performance. It may even be advantageous to have these values programmable on an electrode by electrode basis if there is sufficient processing power to support such a scheme.

The persistence, or decay parameter, is dependent on the individual neural response and by the frequency of stimulation. Generally, higher frequency stimulation generates longer persistence, and greater effect from a given interruption period. Hence, it is highly advantageous to have the stimulation period and interruption period programmable on an individual basis.

While a complete interruption is ideal for resetting the neural response, there are possible alternate embodiments. Any significant change in neural stimulation will tend to reset the neural response. A reduction in signal below threshold will reset the neural response, although a longer time period is required to obtain the desired result. Even a sudden spike in the signal will reset the neural response in some cases.

Figure 5:
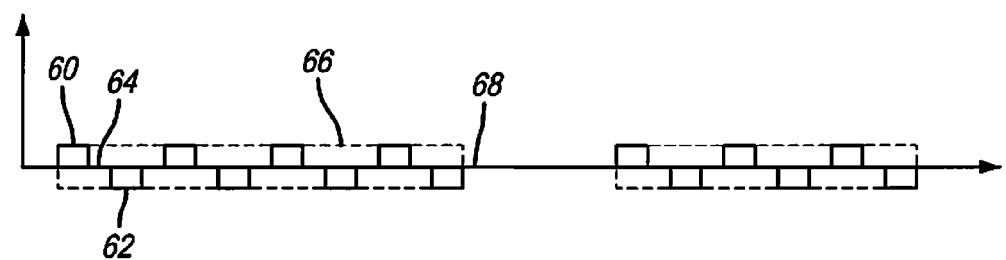
FIG. 5 depicts a stimulation waveform train including interruption.

FIG. 5 depicts a typical pulse sequence stimulation pattern according to the preferred embodiment. The retina is stimulated by biphasic square wave pulses. In the example, a sixty hertz signal with a 33 millisecond interruption is shown. The signal includes cathodic phases 60 and anodic phases 62, with a brief inter-phase interruption 64 between each phases and each pulse, creating a signal envelope 66. The 3 millisecond interruption 68 is an interruption of the signal envelope 66, and should not be confused with the inter-phase interruption 64.

Accordingly, what has been shown is an improved method of making a neural prosthesis and improved method of stimulating neural tissue. While the invention has been described by means of specific embodiments and applications thereof, it is understood that numerous modifications and variations could be made thereto by those skilled in the art without departing from the spirit and scope of the invention. In particular, the preferred embodiment describes a retinal prosthesis for artificial vision. It should be obvious to one skilled in the art that the invention has broad applicability to other types of neural stimulation. It is therefore to be understood that within the scope of the claims, the invention may be practiced otherwise than as specifically described herein.

The invention claimed is:

1. A method of neural stimulation comprising: stimulating neural tissue according to input stimuli by activating electrodes individually or in groups according to a predetermined pattern, wherein the pattern results in interrupting each electrode for a period shorter than the threshold of perception but of sufficient length of time to restore neural sensitivity, and not interrupting all electrodes simultaneously.

2. The method according to claim 1, wherein said predetermined pattern is a pseudorandom pattern.

3. The method according to claim 1, wherein the predetermined pattern is a raster pattern.

4. The method according to claim 1, wherein the predetermined pattern jumps around to avoid sequentially activating geographically nearby electrodes.

5. The method according to claim 1, wherein modifying stimulation on an electrode is reducing stimulation.

6. The method according to claim 1, wherein modifying stimulation on an electrode is not stimulating on the electrode.

7. The method according to claim 1, wherein modifying stimulation is for a period shorter than the threshold of perception.

8. The method according to claim 1, wherein the duration of modifying is programmable.

\* \* \* \* \*